(12) United States Patent
Rowe et al.

(10) Patent No.: US 6,957,958 B2
(45) Date of Patent: Oct. 25, 2005

(54) UNIT DOSE APPLICATOR WITH MATERIAL CHAMBER

(75) Inventors: Gordon Rowe, Wallingford, CT (US); William B. Dragan, Easton, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 10/405,743

(22) Filed: Apr. 2, 2003

(65) Prior Publication Data

US 2004/0197730 A1 Oct. 7, 2004

(51) Int. Cl.⁷ .............................................. A61C 5/04
(52) U.S. Cl. ........................... 433/89; 604/1; 206/209; 206/229; 401/119; 401/126
(58) Field of Search ...................... 433/80, 89; 604/1, 604/2; 206/209, 210, 229; 401/118, 119, 401/126, 129

(56) References Cited

U.S. PATENT DOCUMENTS

| | | | | |
|---|---|---|---|---|
| 3,386,792 | A | * | 6/1968 | Ireland .......................... 401/40 |
| 4,384,645 | A | * | 5/1983 | Manfredi ...................... 206/229 |
| 4,492,305 | A | * | 1/1985 | Avery .......................... 206/210 |
| 4,865,481 | A | * | 9/1989 | Scales .......................... 401/195 |
| 5,001,803 | A | * | 3/1991 | Discko, Jr. .................. 15/167.1 |
| 5,109,979 | A | * | 5/1992 | Cole ............................ 206/229 |
| 5,150,495 | A | * | 9/1992 | Discko et al. .............. 15/167.1 |
| 5,425,591 | A | * | 6/1995 | Contreras et al. ........... 401/191 |
| 5,660,273 | A | * | 8/1997 | Discko, Jr. ................... 206/229 |
| 5,954,996 | A | * | 9/1999 | Discko, Jr. .................. 252/79.1 |
| 6,049,934 | A |   | 4/2000 | Discko |
| 6,059,570 | A |   | 5/2000 | Dragan et al. |
| 6,099,307 | A |   | 8/2000 | Discko, Jr. |
| 6,186,792 | B1 | * | 2/2001 | Discko ........................ 433/220 |
| 6,202,897 | B1 | * | 3/2001 | Martin et al. ................ 222/386 |
| 6,283,933 | B1 |   | 9/2001 | D'Alessio et al. |
| 6,328,159 | B1 |   | 12/2001 | Discko, Jr. |
| 6,372,313 | B1 | * | 4/2002 | D'Alessio et al. ......... 428/34.1 |
| 6,372,816 | B1 | * | 4/2002 | Walz et al. .................. 523/116 |
| 6,382,972 | B1 |   | 5/2002 | Fischer et al. |
| 6,413,087 | B1 | * | 7/2002 | Petrich et al. ............... 433/89 |
| 6,450,717 | B1 |   | 9/2002 | Salz et al. .................... 401/125 |
| 6,516,947 | B1 | * | 2/2003 | Van Dyke et al. .......... 206/361 |
| 6,592,280 | B2 | * | 7/2003 | Petrich et al. .............. 401/126 |
| 6,634,051 | B1 | * | 10/2003 | Dragan et al. ................ 15/106 |
| 6,685,013 | B2 | * | 2/2004 | Discko, Jr. ................... 206/229 |
| 6,758,618 | B2 | * | 7/2004 | Petrich et al. .............. 401/130 |

* cited by examiner

*Primary Examiner*—Ralph A. Lewis
(74) *Attorney, Agent, or Firm*—Fattibene & Fattibene; Paul A. Fattibene; Arthur T. Fattibene

(57) ABSTRACT

An applicator having an applicator end portion and a material end portion. The material end portion forms a container holding a material to be applied with the applicator end portion. Upon separating the material end portion from the handle portion of the applicator, a container is formed which is used to dip the applicator end portion of the applicator into. The present invention is particularly applicable to the dispensing of medicaments, and in particular, dental materials. A single dose of material is integrally formed within the applicator and sealed until ready for use.

19 Claims, 5 Drawing Sheets

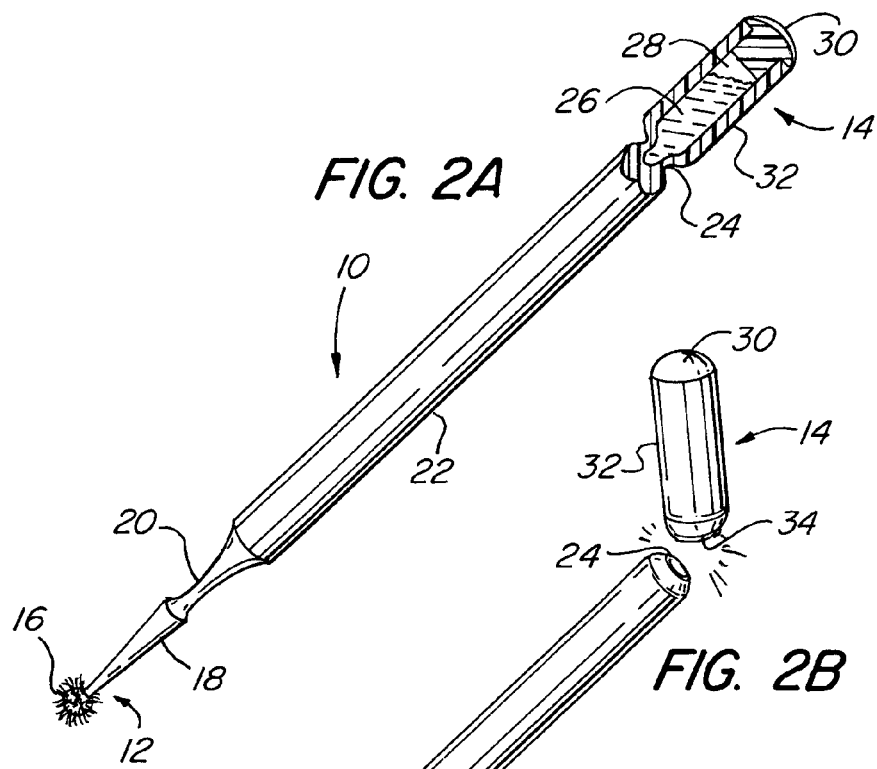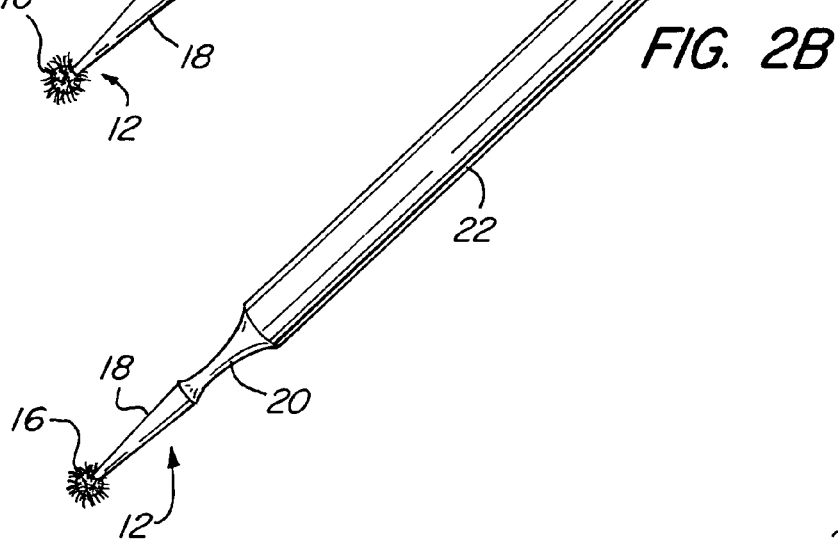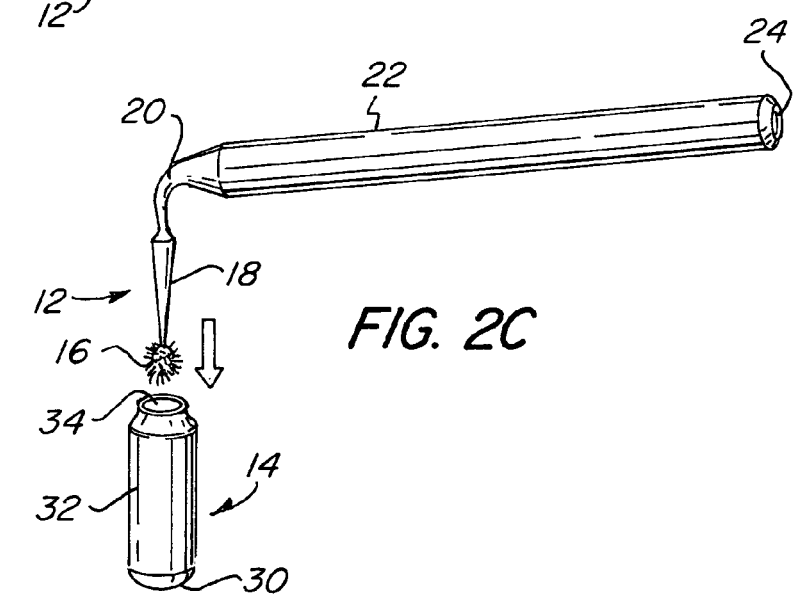

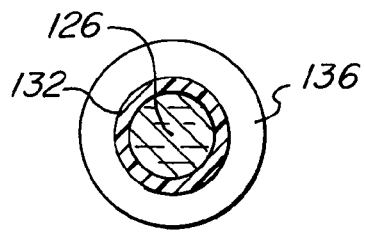
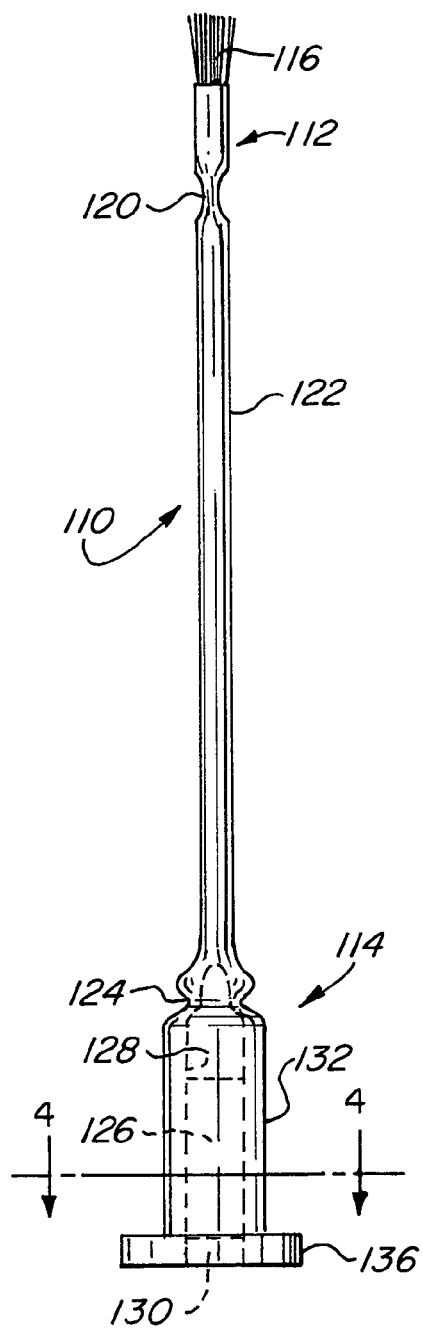
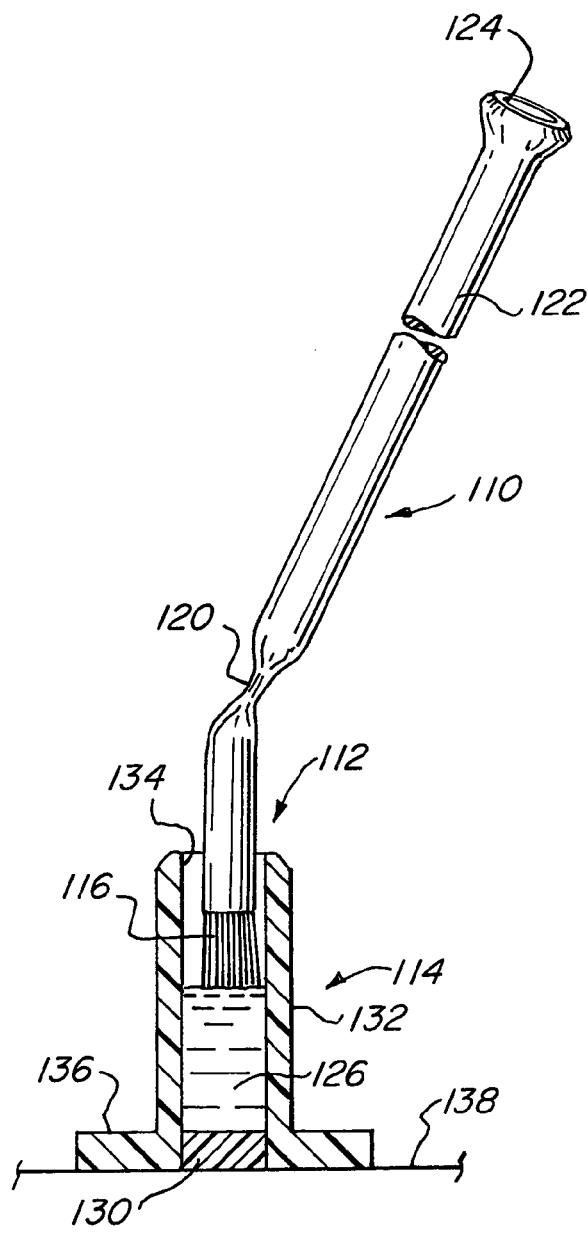
FIG. 4
FIG. 3A
FIG. 3B

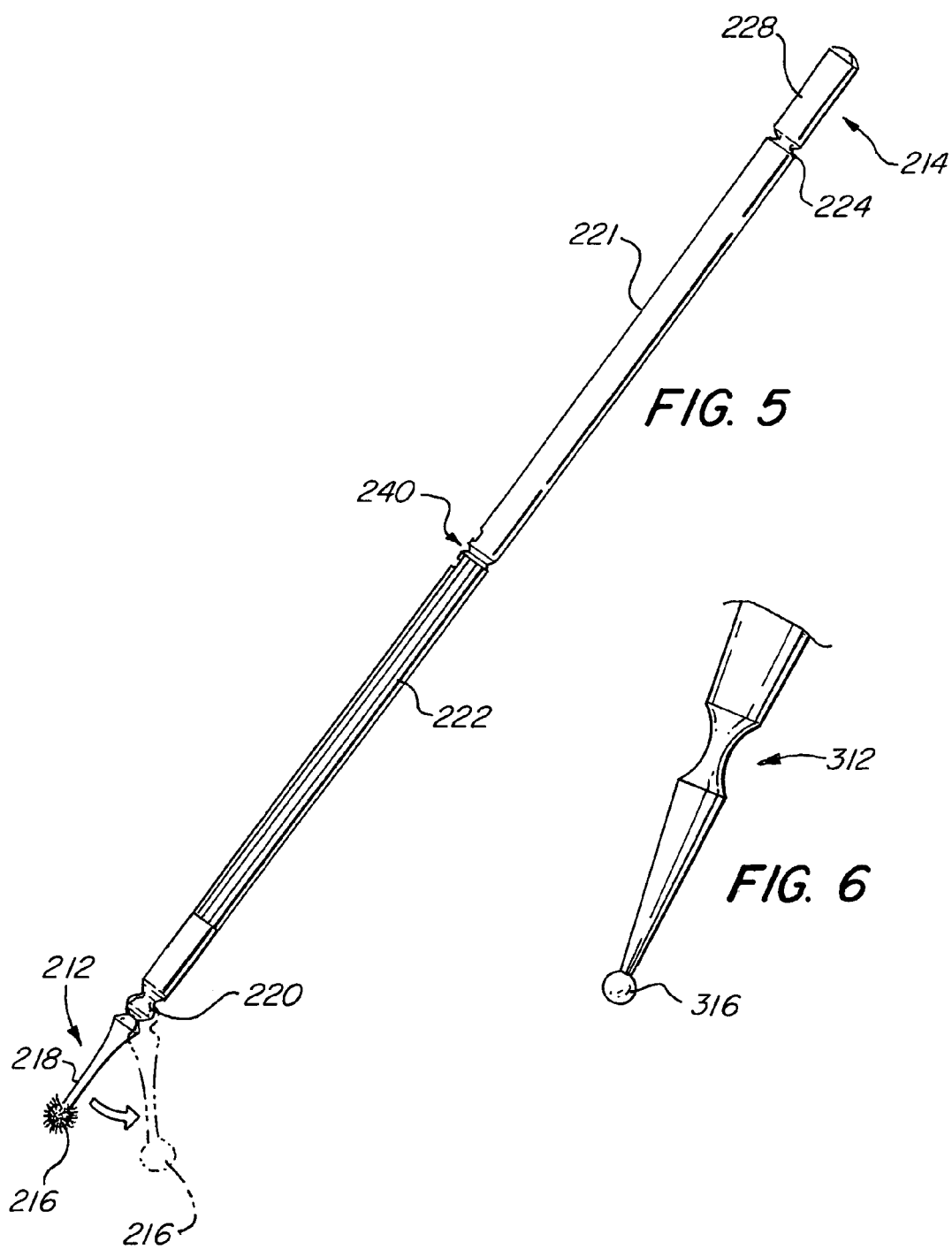

UNIT DOSE APPLICATOR WITH MATERIAL CHAMBER

FIELD OF THE INVENTION

The present invention relates generally to a disposable applicator, and more particularly to an applicator containing a dose of material.

BACKGROUND OF THE INVENTION

There are many different kinds of applicators used to dispense a material applied to a surface. Many of these materials to be applied are medicaments or, in particular, dental materials used during a medical or dental procedure. One such applicator type device containing a material is disclosed in U.S. Pat. No. 6,059,570 entitled "Dental Container Type Applicator" and issuing to Dragan et al on May 9, 2000. Therein disclosed is a dental container type applicator in the form of a capsule. The material is extruded from the capsule and applied with the aid of minute fibers or flocking adhered to the discharge nozzle.

Another applicator type capsule is disclosed in U.S. Pat. No. 6,099,307 entitled "Dental Capsule for Containing and Dispensing Low Viscosity Dental Material and Method of Filing and Applying said Low Viscosity Material" and issuing to Discko, Jr. on Aug. 8, 2000. Therein disclosed is a dental capsule for dispensing low viscosity or liquid like dental materials. A sponge or cellular foam like material is contained within the body portion of the capsule. A displaceable piston is used to compress the saturated sponge or cellular foam like material to dispense the liquid or low viscosity material.

Another applicator for applying a material is disclosed in U.S. Pat. No. 6,382,972 entitled "Cushioned, Fiber-Covered Dental Delivery Tips" issuing to Fischer et al on May 7, 2002. Therein disclosed are various applicators or tips for dispensing or applying a dental material. In one embodiment, a material is contained within a portion of the applicator. Upon displacing a piston like portion of the applicator, a material is forced through a channel and through the tip of the applicator.

While these applicators and devices have been helpful in dispensing a material, they have required an applicator having multiple parts with a displaceable member or piston to dispense the material. While this is desirable for some applications, it may be advantageous to simply dip a brush or applicator into a material to better control the dispensing and application of the material. Accordingly, a brush may often be used as a simple cost effective way to apply a material. One such brush is disclosed in U.S. Pat. No. 6,049,934 entitled "Disposable Dental Applicator" and issuing to Discko on Apr. 18, 2000. Therein disclosed is an applicator having two ends which may be broken to form two separate independent applicators. The applicator may then be used to apply a material. This is a very cost effective and simple applicator. However, it is inconvenient in that the material cannot be conveniently stored with the applicator. A solution to this problem is disclosed in U.S. Pat. No. 6,328,159 entitled "Single Patient Dose Medicament Dispenser with Applicator" and issuing to Discko, Jr. on Dec. 11, 2001. Therein disclosed is an applicator held in a material dispensing tray which contains a material to be dispensed. The tray has a cover protecting the applicator and the material. While the material is contained with the applicator, the package is relatively bulky and difficult to store and ship in large quantities.

Another applicator is disclosed in U.S. Pat. No. 6,283,933 entitled "Applicator For Dispensing Liquids" and issuing to D'Alessio et al on Sep. 4, 2001. Therein disclosed is an applicator having a breakable ampule containing a material held therein. Upon squeezing the body portion of the applicator, the ampule breaks, releasing the liquid contained therein. The liquid then travels through the interior of the applicator to an applicator swab for application.

Although these applicators have adequately applied various different materials, they are not within disadvantages. Some of the applicators have multiple parts and are relatively expensive to manufacture. Other applicators are relatively large and difficult to store or package in large quantities.

In the manufacture of disposable applicators intended for a single use, it is important that the applicator be simple and easy to manufacture, and that provides little waste of applicator material or material to be dispensed. Therefore, there is a need to provide an applicator that contains a single dose of material that is easily and inexpensively manufactured and shipped together.

SUMMARY OF THE INVENTION

The present invention is a disposable applicator package that has a chamber therein formed on one end for containing a dose of material that is easily made accessible for dispensing with the applicator formed on another end. An elongated handle has an applicator end formed thereon. At the other end, a material end is formed. The material end has a chamber containing a material for dispensing. The material is initially sealed within the material end of the applicator package. A frangible portion separates the material end of the applicator from the handle of the applicator package. Upon separation of the material end from the handle of the applicator package, the chamber containing the material in the material end is opened, permitting the applicator end to be dipped therein.

Accordingly, it is an object of the present invention to provide an applicator package that is simple and easy to manufacture.

It is a further object of the present invention to provide a self contained applicator package for holding a dose of material to be dispensed.

It is an advantage of the present invention that a single dose of material for dispensing is safely stored and is made easily accessible.

It is a further advantage of the present invention that it is easily packaged and stored in a large number of individual units in a small volume of space.

It is a feature of the present invention that the material is sealed within a chamber at one end of the applicator package.

It is another feature of the present invention that a frangible portion adjacent the material end of the applicator package permits the material end to be separated from the applicator end, making accessible the material to be applied with the applicator end.

These and other objects, advantages, and features will become readily apparent in view of the following more detailed description.

BRIEF DESCRIPTION OF THE DRAWINGS

FIG. 2A is a partial cross section illustrating a material contained within the material end of the applicator package.

FIG. 2B illustrates the removal of the material end containing the material to be applied.

FIG. 2C illustrates the placement of the material contained in the material end to the applicator end of the applicator package.

FIG. 3A is an elevational view illustrating another embodiment of the present invention having a larger material end and a support flange.

FIG. 3B is a partial cross section illustrating the placement of a material onto the separated applicator end, utilizing the material end of the applicator package.

FIG. 4 is a cross section taken along line 4—4 in FIG. 3A.

FIG. 5 is a side elevational view illustrating another embodiment of the present invention having a second frangible portion.

FIG. 6 is a partial view illustrating the applicator end of another embodiment of the present invention.

DETAILED DESCRIPTION OF THE PREFERRED EMBODIMENTS

Figure 1:
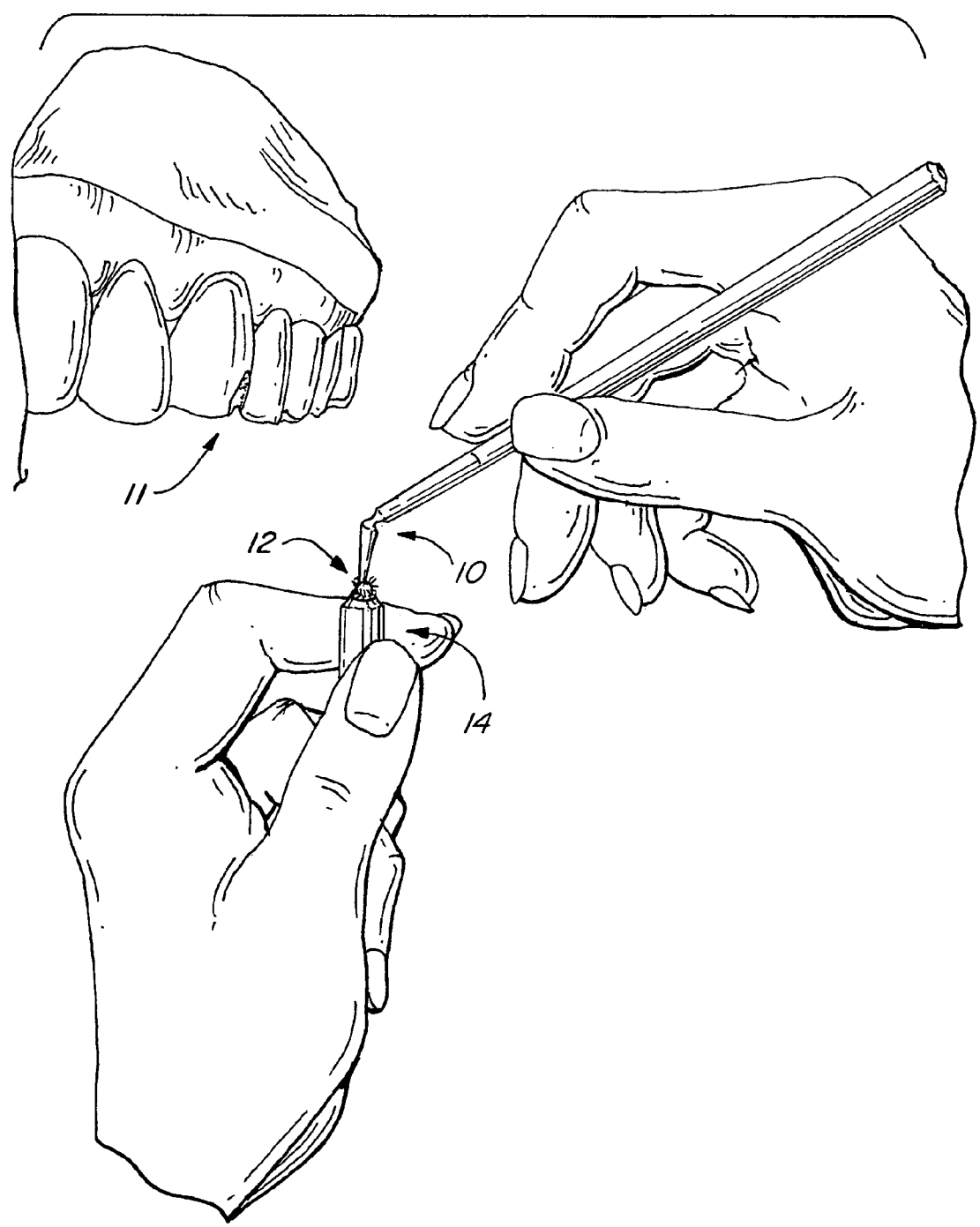
FIG. 1 illustrates the use of the present invention in applying a dental material.

FIG. 1 illustrates the use of the applicator package of the present invention. In FIG. 1, the applicator package 10 has an applicator end or portion 12. The applicator end or portion 12 is placed within the separated material end or portion 14 containing a material to be applied. In this example, a dental material contained within the material end or portion 14 is being applied to teeth 11 of a patient's mouth.

FIGS. 2A–C illustrate and embodiment of the present invention. FIG. 2A illustrates the applicator package 10 having an applicator end or portion 12 and a material end or portion 14. The applicator end or portion 12 has flock 16 formed thereon. The applicator end or portion 12 may also contain any other applicator material, such as foam, brush bristles, cotton, or other equivalent applicator material. Tapered portion 18 extends from the flock 16 to a bendable neck 20. The bendable neck 20 permits the tapered portion 18 to be bent relative to the handle portion 22. This facilitates the application of the material in areas that may otherwise be difficult to reach. At the other end of the handle portion 22 is a breakable or frangible portion 24. The frangible portion 24 may be any weakened area, such as a scribe line or an indentation within the handle portion 22 that facilitates easy separation of the material end or portion 14 from the handle portion 22. The frangible portion 24 may also be a groove circumscribing the perimeter of the applicator device 10. Placed within the material end or portion 14 is a material chamber 28. Contained within the material chamber 28 is a material 26. The material 26 may be any material such as a liquid, gel, paste, powder or other equivalent material that is intended to be dispensed with the applicator end or portion 12. The material is initially sealed within the material chamber 28 by the end of the handle portion 22 just past the frangible portion 24 and end seal 30. The applicator package 10 may be made by any conventional manufacturing process such as extrusion or molding and is preferably made of an inexpensive plastic material. The material 26 may also be placed in the material chamber 28 by any conventional technique. One technique is simply to mold the applicator package 10 with the material chamber 28 having an open end which can be sealed with a plug or seal 30 after placement of the material 26 therein. The end seal 30 may be glued, thermally, or sonically welded in place to effectively seal the material chamber 28.

FIG. 2B illustrates the separation of the material end portion 14 from the handle portion 22. The frangible portion 24 permits the material end portion 14 to be easily separated from the handle portion 22. The frangible portion 24 may be a scribe line, groove, or any other weakened portion that permits easy separation. Simply bending the material end portion 14 and the handle portion 22 results in the snapping or breaking of the frangible portion 24. As a result, an opening or mouth 34 is formed within the container 32 of the material end portion 14. The container 32 holds the material 26 within the chamber 28 illustrated in FIG. 2A.

FIG. 2C illustrates the placement of material contained within the material end portion 14 on the applicator end portion 12. The flock 16 on the tapered portion 18 of the applicator end portion 12 is dipped through the mouth or opening 34 of container 32 to be coated with the material contained therein. The tapered portion 18 between the flock 16 and the neck 20 should have a length greater than the depth of the container 32. This will permit the applicator end 12 with flock 16 to be inserted to the bottom of the container 32 even when the neck 20 is positioned so that the tapered portion 18 is angularly disposed relative the handle portion 22. The application of the amount of material applied can easily be controlled. Additionally, more material can be applied to the applicator end portion 12 by re-dipping the applicator end portion 12 within the container 32 without the need to worry about cross contamination between patients. Therefore, the present invention permits better control than prior self-contained applicators having material to be dispensed contained therein. The present invention combines the benefits of using a bulk container to dispense a material with the single dose disposable features of other, less controllable applicators that contain a dose of material.

FIGS. 3A and 3B illustrate another embodiment of the present invention. In this embodiment, a support flange is formed on the material end, permitting the material end to be self-supporting in an upright position on a surface. The applicator 110 has an applicator end portion 112 and a material end portion 114. The applicator end portion 112 contains bristles 116 in this embodiment. However, it should be appreciated that any material can be used suitable for use as an applicator. A neck 120 is formed between the applicator end portion and a handle 122. At the other end of the handle 122 is a frangible portion 124. The frangible portion 124 permits separation of the handle portion 122 from the material end portion 114. The material end portion 114 forms a container 132 having a material chamber 128 formed therein. The material chamber 128 contains a material 126. An end seal 130 seals the material chamber 128 opposite the handle portion 122. Therefore, before use the material is completely sealed within the material chamber 128.

A support flange or base 136 is formed around an end of the container 132. The material end portion 114 may have a diameter larger than the handle portion 122. The diameter of the material end portion 114 may be made any convenient size so as to accommodate the expected single dose quantity of material contained therein. Additionally, while this embodiment has been illustrated with an applicator end portion 112 having bristles 116 therein, clearly it should be appreciated that any applicator material can be used in any of the embodiments illustrated. For example, instead of bristles 116, flock, foam, cotton, or any other applicator material may be used.

FIG. 3B illustrates the use of the applicator 110 once the material end portion 114 has been separated from the handle portion 122. Upon separation of the handle portion 122 from the material end portion 114, the material end portion 114 may be placed on a surface 138. The support flange or base 136 stabilizes the material end portion 114 on the surface 138. Accordingly, the opened material end portion 114 can be left on a surface without falling over and spilling the material 126 contained therein. Once the material end portion 114 is removed from the handle 122, opening 134 is formed. The applicator end portion 112 and the bristles 116 can then be placed through the opening 134 to access the material 126. The material 126 can then be applied to a patient.

FIG. 4 is a cross section taken along line 4—4 in FIG. 3A. The walls of the container 132 and the support flange or base 136 are illustrated. The material 126 is contained within the container 132.

In the embodiment illustrated in FIGS. 3A, 3B, and 4 a larger material end 114 is used that is capable of containing more material 126. The material end 114 has a diameter or lateral dimension greater than the diameter or lateral dimension of the applicator end or portion 112.

FIG. 5 illustrates another embodiment of the present invention. In this embodiment, a second frangible portion 240 is placed between an applicator handle portion 222 and a material handle portion 221. The material end portion 214 is placed adjacent the material handle portion 221. The material end portion 214 is capable of being separated from the material handle portion 221 by a frangible portion 224. The material chamber 228 is formed within the material end portion 214 and is made accessible upon breaking the frangible portion 224. The applicator end portion 212 has a tapered portion 218, a neck 220, and flocking 216 thereon. Neck 220 permits bending as illustrated in phantom. The second frangible portion 240 permits the applicator end portion 212 to be separated from the material end portion 214 prior to opening the material chamber 228 by separating the material handle portion 221 therefrom.

FIG. 6 illustrates another applicator end portion 312 with a ball 316 end. The ball 316 end is formed from a sphere of plastic material. In some applications, a ball applicator may be desired. Typically, a ball applicator could be used for application of liquids. The ball applicator contains or holds the material yet is not absorbent.

Figure 7:
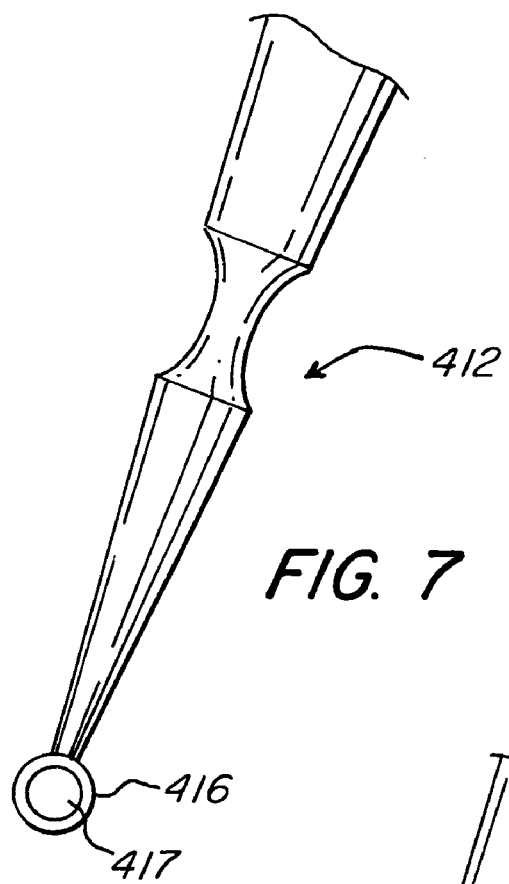
FIG. 7 is a partial view illustrating the applicator end of another embodiment of the present invention.

FIG. 7 illustrates another applicator end portion 412 with a loop 416 formed with a hole 417. The applicator end portion 412 is capable of holding and applying liquids without being absorbent.

Figure 8:
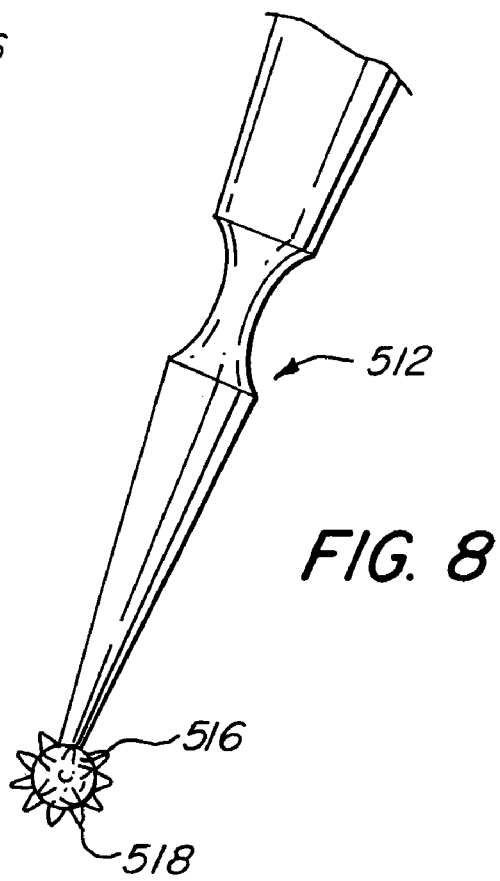
FIG. 8 is a partial view illustrating the applicator end of another embodiment of the present invention.

FIG. 8 illustrates another applicator end portion 512 with a mace-shaped end. The mace-shaped end is formed from a round end 516 having extending radially spikes or protrusions 518. Applicator end portion 512 is beneficial in holding liquids as well as other materials that are desired to be used in combination with a stimulating effect from rubbing or burnishing.

While the present invention may be used for applying any material, it is particularly applicable to the medical field and, in particular, dentistry. The applicator is relatively inexpensive to manufacture, may be stored in large quantities within a small space and is well suited to a single dose of material, preventing cross-contamination. The applicator is intended for a single use only. The applicator is well suited to dental materials, and in particular bonding agents, sealers, desensitizing material, hemostatic agents, astringents, adhesives, and other materials that can be brushed or painted on.

While the present invention has been described with respect to the preferred embodiments, it should be appreciated by those skilled in the art that various modifications may be made without departing from the spirit and scope of this invention.

What is claimed is:

1. An applicator device containing a material for dispensing comprising:
   an elongated handle having an applicator end and a material end;
   an applicator formed on said applicator end;
   a neck placed between said elongated handle and said applicator end, whereby said applicator is capable of being angularly disposed relative to said handle;
   a material chamber formed in the material end of said elongated handle and containing the material, said material chamber being initially sealed between said elongated handle and the material end; and
   a frangible portion integrally formed within a wall of said elongated handle and placed between said elongated handle and said material end,
   whereby upon separating said material end from said elongated handle an opening is formed in said material chamber permitting said applicator to be placed within said material chamber and the material to be applied with said applicator.

2. An applicator device containing a material for dispensing as in claim 1 wherein:
   said applicator is spaced from said neck an axial distance greater than an axial depth of said material chamber,
   whereby said applicator is capable of being inserted into said material chamber when said applicator is angularly disposed relative to said handle.

3. An applicator device containing a material for dispensing as in claim 1 wherein:
   said frangible portion is a groove.

4. An applicator device containing a material for dispensing as in claim 1 wherein:
   said applicator comprises a flocked applicator.

5. An applicator device containing a material for dispensing as in claim 1 wherein:
   said applicator comprises a bristle brush applicator.

6. An applicator device containing a material for dispensing as in claim 1 wherein:
   said applicator comprises a ball applicator.

7. An applicator device containing a material as in claim 1 wherein:
   said applicator comprises a loop applicator.

8. An applicator device containing a material as in claim 1 wherein:
   said applicator comprises a round portion having protrusions.

9. An applicator device containing a material for dispensing as in claim 1 wherein:
   the material is a dental material.

10. An applicator device containing a material comprising:
    an applicator handle portion;
    an applicator attached to said applicator handle portion;
    a material handle portion initially attached to said applicator handle portion;
    a first frangible portion placed between said applicator handle portion and said material handle portion, whereby said applicator handle portion is capable of being separated from said material handle portion;

a material portion initially attached to said material handle portion, said material portion having a material chamber containing the material; and a second frangible portion placed between said material handle portion and said material portion, whereby said material handle portion is capable of being separated from said material portion exposing the material permitting the applicator to be used to apply the material.

11. An applicator device containing a material as in claim 10 wherein:

said applicator comprises a flocked applicator.

12. An applicator device containing a material as in claim 10 wherein:

said applicator comprises a ball applicator.

13. An applicator device containing a material as in claim 10 wherein:

said applicator comprises a bristle brush applicator.

14. An applicator device containing a material as in claim 10 wherein:

said applicator comprises a loop applicator.

15. An applicator device containing a material as in claim 10 wherein:

said applicator comprises a round portion having protrusions.

16. An applicator device containing a material as in claim 10 wherein:

said frangible portion comprises a groove circumscribing the applicator device.

17. A method of applying a material comprising the steps of:

forming an applicator handle having an applicator end and a material end so that the applicator handle is between the applicator end and the material end;

sealing the material in the material end of the applicator handle;

forming a frangible portion between the applicator handle and said material end;

separating the material end from the applicator handle along the frangible portion forming an opening in the material end exposing the material; and inserting the applicator end into said material end, whereby a predetermined dose of material is capable of being applied.

18. An applicator device containing a material comprising:

a handle portion having an applicator end and a material end, the applicator end and the material end being separated by said handle portion;

an applicator attached to said handle portion on the applicator end, said applicator comprising a loop applicator; and an initially sealed material portion frangibly attached to said handle portion on the material end, whereby when said material portion is separated from said handle portion the material is exposed.

19. An applicator device containing a material comprising:

an elongated handle having an applicator end and a material end, said elongated handle positioned between the applicator end and the material end;

an applicator formed on said applicator end, said applicator comprising a loop applicator;

a material container attached to said material end, said material container having an initially sealed chamber holding the material; and a frangible portion integrally formed within said elongated handle separating said elongated handle and said material container, whereby upon separating said material container from said elongated handle an opening is toned in said material container permitting application of the material with said applicator.

* * * * *